(12) United States Patent
Stott et al.

(10) Patent No.: US 9,048,076 B2
(45) Date of Patent: Jun. 2, 2015

(54) NON-CONTACT TRACE CHEMICAL SCREENING

(75) Inventors: William R. Stott, King (CA); Gholamreza Javahery, Kettleby (CA)

(73) Assignee: MSDetection Corp., Bolton (CA)

( * ) Notice: Subject to any disclaimer, the term of this patent is extended or adjusted under 35 U.S.C. 154(b) by 0 days.

(21) Appl. No.: 14/122,534

(22) PCT Filed: May 25, 2012

(86) PCT No.: PCT/CA2012/000505
§ 371 (c)(1),
(2), (4) Date: Jan. 8, 2014

(87) PCT Pub. No.: WO2012/162795
PCT Pub. Date: Dec. 6, 2012

(65) Prior Publication Data
US 2014/0117223 A1    May 1, 2014

Related U.S. Application Data

(60) Provisional application No. 61/490,807, filed on May 27, 2011.

(51) Int. Cl.
| | |
|---|---|
| *H01J 49/04* | (2006.01) |
| *H01J 49/00* | (2006.01) |
| *G01N 1/22* | (2006.01) |
| *G01N 1/24* | (2006.01) |

(Continued)

(52) U.S. Cl.
CPC .............. *H01J 49/04* (2013.01); *H01J 49/00* (2013.01); *G01N 1/22* (2013.01); *G01N 1/24* (2013.01); *H01J 49/02* (2013.01); *G01N 2001/024* (2013.01); *H01J 49/0459* (2013.01); *G01N 2001/022* (2013.01)

(58) Field of Classification Search
CPC .............. G01N 2001/022; G01N 2001/024; G01N 1/24; G01N 2001/028; G01N 2001/2241; G01N 27/622; G01N 1/22; G01N 33/0057; H01J 49/04; H01J 49/40; H01J 49/00; H01J 49/02; H01J 49/10
USPC ................................................ 250/281–300
See application file for complete search history.

(56) References Cited

U.S. PATENT DOCUMENTS

| | | |
|---|---|---|
| 4,580,440 A | 4/1986 | Reid et al. |
| 4,849,628 A | 7/1989 | McLuckey et al. |

(Continued)

OTHER PUBLICATIONS

Chen et al., "Neutral desorption sampling of biological surfaces for rapid chemical characterization by extractive electrospray ionization mass spectrometry," 2008, Nature Protocols, vol. 3, No. 9, pp. 1467-1475.

*Primary Examiner* — Michael Logie

(57) ABSTRACT

Methods and devices for detecting a target substance on a subject without contacting the subject are disclosed. At least one air jet blows analyte from a surface of the subject into an airflow, the airflow entraining the analyte. A desorption channel desorbs molecules from analyte in a portion of the airflow travelling through the desorption channel. An ionizer forms ions from vapor molecules in the portion of the airflow. At least one mass spectrometer analyzes the ions to detect the target substance. The flow travels without interruption from the subject to the at least one mass spectrometer. The desorption channel causes a sufficient quantity of molecules to desorb from the analyte to enable the at least one mass spectrometer to detect the target substance.

27 Claims, 8 Drawing Sheets

(51) Int. Cl.
*H01J 49/02* (2006.01)
*G01N 1/02* (2006.01)

(56) References Cited

U.S. PATENT DOCUMENTS

| | | | |
|---|---|---|---|
| 4,987,767 A * | 1/1991 | Corrigan et al. | 73/23.36 |
| 5,092,155 A * | 3/1992 | Rounbehler et al. | 73/23.41 |
| 5,109,691 A * | 5/1992 | Corrigan et al. | 73/23.36 |
| 5,345,809 A * | 9/1994 | Corrigan et al. | 73/23.2 |
| 5,915,268 A * | 6/1999 | Linker et al. | 73/23.2 |
| 6,037,587 A | 3/2000 | Dowell et al. | |
| 6,073,499 A * | 6/2000 | Settles | 73/864.81 |
| 6,291,821 B1 * | 9/2001 | Danylewych-May et al. | 250/286 |
| 6,610,977 B2 | 8/2003 | Megerle | |
| 6,708,572 B2 | 3/2004 | Jenkins et al. | |
| 6,790,249 B2 | 9/2004 | Davies | |
| 6,848,325 B2 | 2/2005 | Parmeter et al. | |
| 6,894,276 B1 | 5/2005 | Takada et al. | |
| 7,002,145 B2 | 2/2006 | Ishikawa et al. | |
| 7,326,926 B2 | 2/2008 | Wang | |
| 7,401,498 B2 | 7/2008 | Syage et al. | |
| 7,408,153 B2 | 8/2008 | Nagano et al. | |
| 7,458,283 B2 | 12/2008 | Nacson et al. | |
| 8,429,987 B1 * | 4/2013 | Linker et al. | 73/864.33 |
| 2003/0070913 A1 * | 4/2003 | Miller et al. | 204/192.1 |
| 2005/0073683 A1 | 4/2005 | Gard et al. | |
| 2005/0217392 A1 * | 10/2005 | Luke et al. | 73/863.11 |
| 2006/0196249 A1 * | 9/2006 | Syage et al. | 73/31.07 |
| 2008/0250877 A1 * | 10/2008 | Wu | 73/864.33 |
| 2009/0155926 A1 * | 6/2009 | Ovadia et al. | 436/177 |
| 2009/0161824 A1 | 6/2009 | Jenkins | |
| 2010/0294923 A1 * | 11/2010 | Kenny et al. | 250/282 |
| 2010/0301209 A1 | 12/2010 | Ouyang et al. | |
| 2011/0127421 A1 * | 6/2011 | Finlay | 250/283 |

\* cited by examiner

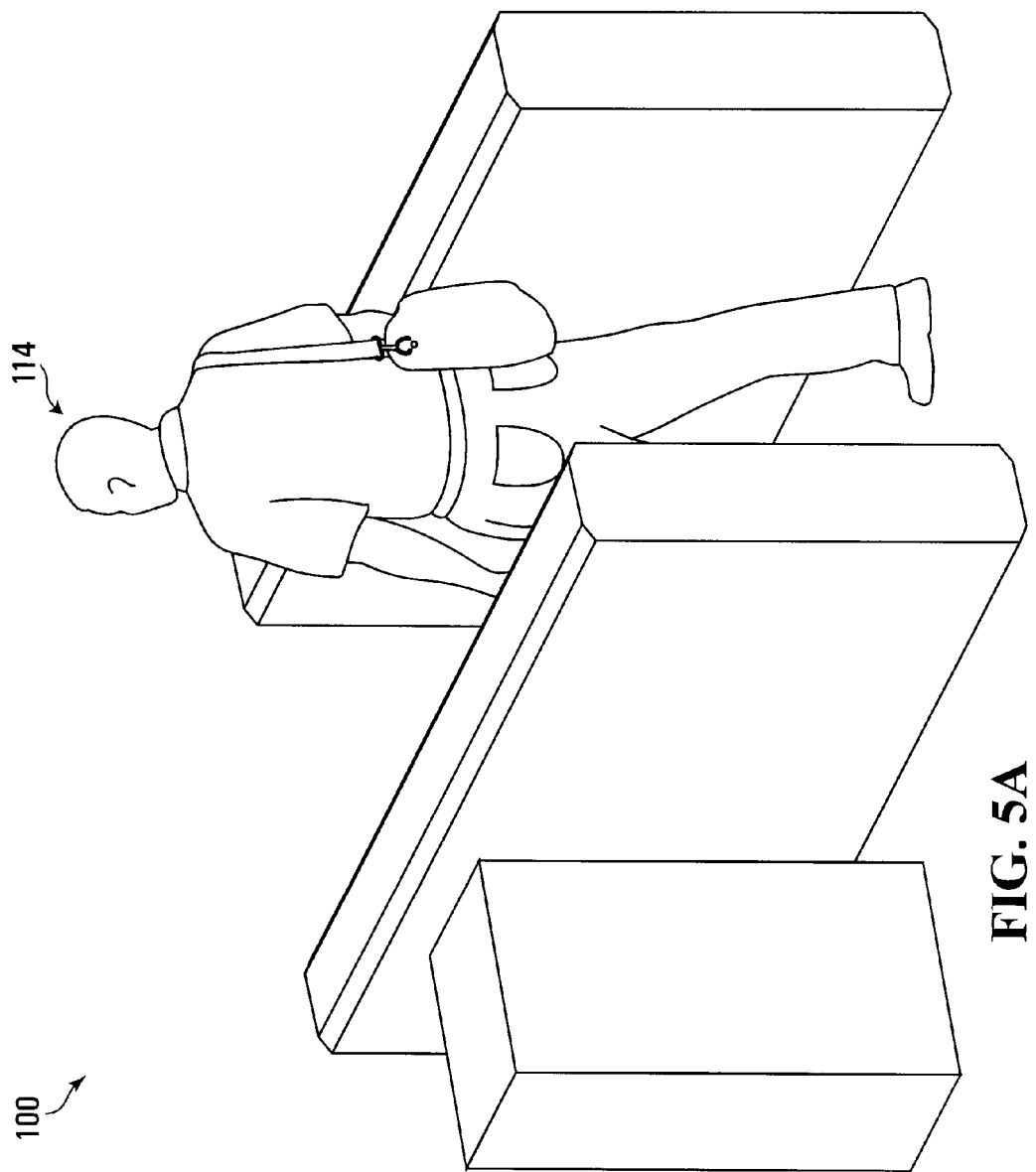

NON-CONTACT TRACE CHEMICAL SCREENING

CROSS-REFERENCE TO RELATED APPLICATION

This application is a national filing of International Application No. PCT/CA2012/000505 filed on May 27, 2012, entitled "NON-CONTACT TRACE CHEMICAL SCREENING", having as inventors William R. Stott and Gholamreza Javahery, which claims benefit of U.S. Provisional Application No. 61/490,807, filed on May 27, 2011, the entire contents of which are incorporated herein by reference.

FIELD OF THE INVENTION

The present invention relates to non-contact trace chemical screening to detect residues of target substances, such as, for example, narcotics, explosives, poisons or the like. More specifically, the present invention relates to a device for non-contact trace chemical screening, and a detection method.

BACKGROUND OF THE INVENTION

At many locations, maintaining security of access requires screening subjects who enter the location for contraband substances. For example, at airports, passengers and luggage are screened for narcotics and explosives. Similar screening is performed at other locations where security of access is important, such as train stations, border crossings, public buildings, government offices, sporting facilities, tourist attractions, mail depots, etc. The subjects to be screened may be persons, parcels, packages, baggage, electronic devices, tickets, and any other subjects which may have come into contact with a target substance.

At locations where subjects must pass through at a high rate, screening may create a bottleneck. It is therefore desirable at such locations to screen subjects quickly. It is also often desirable to screen subjects in a minimally-intrusive way to avoid any unnecessary invasion of privacy.

Trace chemical screening devices detect a target substance, such as a narcotic or an explosive chemical, based on the presence of minute quantities of molecules or ions from residues of the target substance. Thus, compared to metal detectors which screen only for metallic contraband such as weapons, and x-ray machines which screen based on bulk shapes that resemble contraband, trace chemical screening devices may be used to screen for a broader range of target substances, while performing screening at greater sensitivity and selectivity. Trace chemical screening devices may therefore be used in place of, or in conjunction with conventional detection devices such as metal detectors and x-ray machines.

An exemplary trace chemical screening devices is disclosed in U.S. Pat. No. 7,458,283 to Nacson et al. According to Nacson et al, analyte is sampled from the subject by wiping the surface of the subject with a swab. The device then uses a spectrometer to analyze swabbed analyte to determine if a target substance is present.

Trace chemical screening devices which screen subjects without requiring any physical contact with the subject, and are therefore less intrusive than the device disclosed in Nacson et al., are also known. Exemplary non-contact trace chemical screening devices are disclosed in U.S. Pat. No. 5,915,268 to Linker et al. and U.S. Pat. No. 6,610,977 to Megerle. According to Linker et al. and Megerle, analyte is collected from a subject by blowing air onto the subject to entrain analyte into an airflow. Analyte may include residues of the target substance in particle or vapour form. The airflow containing the analyte is sampled, and a detector is used to analyze analyte within the sampled air to determine if a target substance is present. Linker et al. and Megerle disclose a variety of detectors, including detectors which perform detection using ion mobility spectrometry, electron capture detection, and gas chromatography/chemiluminescence.

One problem associated with conventional non-contact trace chemical screening devices lies in providing a detectable concentration of the target substance to the detector. The concentration of the target substance carried in the sampled air may often fall below the detector's sensitivity threshold. As such, a preconcentrator may be used to increase the concentration of the target substance to level above the detector's sensitivity threshold.

However, when a preconcentrator is used, sampled air containing analyte is not provided directly to the detector. Rather, sampled air is first passed through the preconcentrator, which forms a concentrated sample by accumulating analyte from the sampled air over time. For example, the preconcentrator may include an activated carbon filter to absorb analyte from sampled air passing through the preconcentrator.

After the preconcentrator accumulates a sufficient quantity of analyte, the concentration of the target substance in the concentrated sample is increased to a level above the detector's sensitivity threshold. The concentrated sample is then provided to the detector to detect the target substance.

While a preconcentrator enables non-contact trace chemical screening devices to detect low concentrations of the target substance in sampled air, the use of a preconcentrator introduces a number of problems. Firstly, the use of a preconcentrator may consume materials such as activated carbon, thereby increasing operational costs. Secondly, the use of a preconcentrator increases screening time per subject, as additional time spent accumulating sufficient quantity of analyte, thereby reducing detection throughput.

Accordingly, there remains need for an improved non-contact chemical screening device.

SUMMARY OF THE INVENTION

In an aspect of the present invention, there is provided a device for detecting a target substance on a subject without contacting the subject. The device includes at least one air jet for blowing analyte from a surface of the subject into an airflow, the airflow entraining the analyte; an inlet for receiving at least a portion of the airflow; a desorption channel in fluid communication with the inlet for desorbing molecules from analyte in the portion of the airflow travelling through the desorption channel; an ionizer, in fluid communication with the desorption channel, for forming ions from vapour molecules in the portion of the airflow; and at least one mass spectrometer in fluid communication with the ionizer, for analyzing the ions to detect the target substance. The airflow travels without interruption from the subject to the at least one mass spectrometer. The desorption channel causes a sufficient quantity of molecules to desorb from the analyte to enable the at least one mass spectrometer to detect the target substance.

In a further aspect of the present invention, there is provided a method of detecting a target substance on a subject without contacting said subject. The method includes blowing analyte from a surface of the subject into an airflow, the airflow entraining the analyte; desorbing molecules from the analyte in the airflow, while the airflow travels without interruption from the subject to a tandem quadrupole mass spectrometer; ionizing vapour molecules in the airflow to form ions; and analyzing said ions using at least one mass spectrometer to detect the target substance.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures which illustrate by way of example only, embodiments of the present invention.

FIG. 5A is a perspective view of a non-contact trace chemical screening device for detecting a target substance on a person, exemplary of another embodiment of the present invention.

Figure 1:
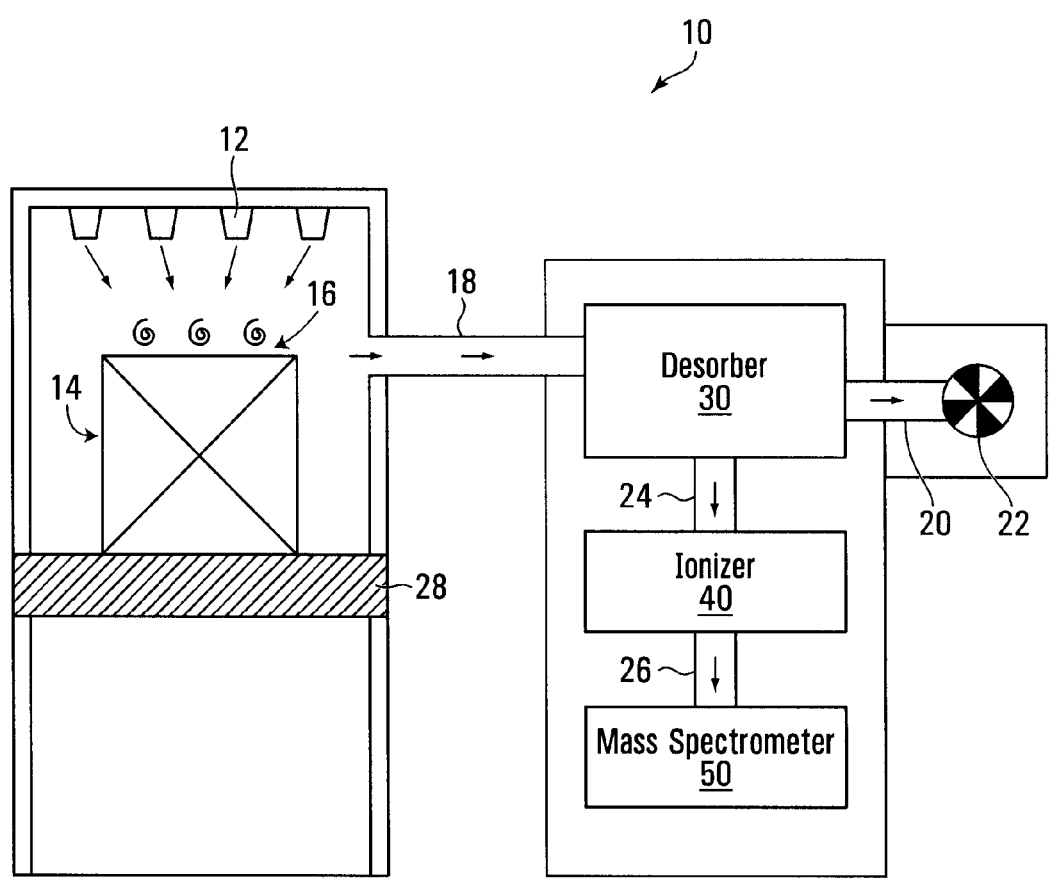
FIG. 1 is a schematic diagram of a non-contact trace chemical screening device for detecting a target substance on a package, exemplary of an embodiment of the present invention.

In the drawings, preferred embodiments of the invention are illustrated by way of example. It is to be expressly understood that the description and drawings are for the purpose of illustration and as an aid to understanding, and are not intended as a definition of the limits of the invention.

DETAILED DESCRIPTION

FIG. 1 shows a non-contact trace chemical screening device 10, exemplary of an embodiment of the present invention. Non-contact trace chemical screening device 10 may be used to detect a target substance on packages such as package 14. Device 10 includes a conveyer belt 28 for carrying packages through a detection area; a plurality of air jets 12 in the detection area for blowing analyte from package 14 into an airflow; a desorber 30 for desorbing molecules from analyte carried in the airflow through desorber inlet 18; a fan 22 for drawing the airflow through desorber 30, and for exhausting waste airflow from desorber 30 out of device 10; an ionizer 40 for ionizing vapour molecules in a portion of the airflow received from desorber 30; and a mass spectrometer 50 for analyzing ions in the portion of airflow received from ionizer 40 to detect the target substance.

Air jets 12 are selected to blow air with sufficient pressure to lift analyte from the surface of package 14. Any of air jets 12 may of a conventional variety, such as AiRTX® Model 48009, capable of blowing air with pressure in the range of 40 psi to 100 psi.

In the embodiment depicted in FIG. 1, four air jets 12 are used. A fewer or greater number of air jets 12 may also be used. A person skilled in the art will understand that in some embodiments, a single air jet may be sufficient to lift analyte from the surface of package 14.

As depicted in FIG. 1, air jets 12 are disposed at the top of the detection area to blow air downwards at package 14 from a distance of approximately 100 mm to 500 mm. Air jets 12 may also be disposed elsewhere around the perimeter of the detection area, for example, to blow air at package 14 from the sides or from the bottom of the detection area. The distance between air jets 12 and package 14 may also be varied, so long as sufficient pressure is applied to lift analyte from the surface of package 14.

Fan 22 is selected to draw a sufficient volume of air carrying analyte from package 14 through desorber 30 for a sufficient quantity of molecules of the target substance to desorb from the analyte for detection. Fan 22 may of a conventional variety, such as GAST® Blower R4P115 which operates at approximately 50 rpm to 60 rpm.

Figure 2:
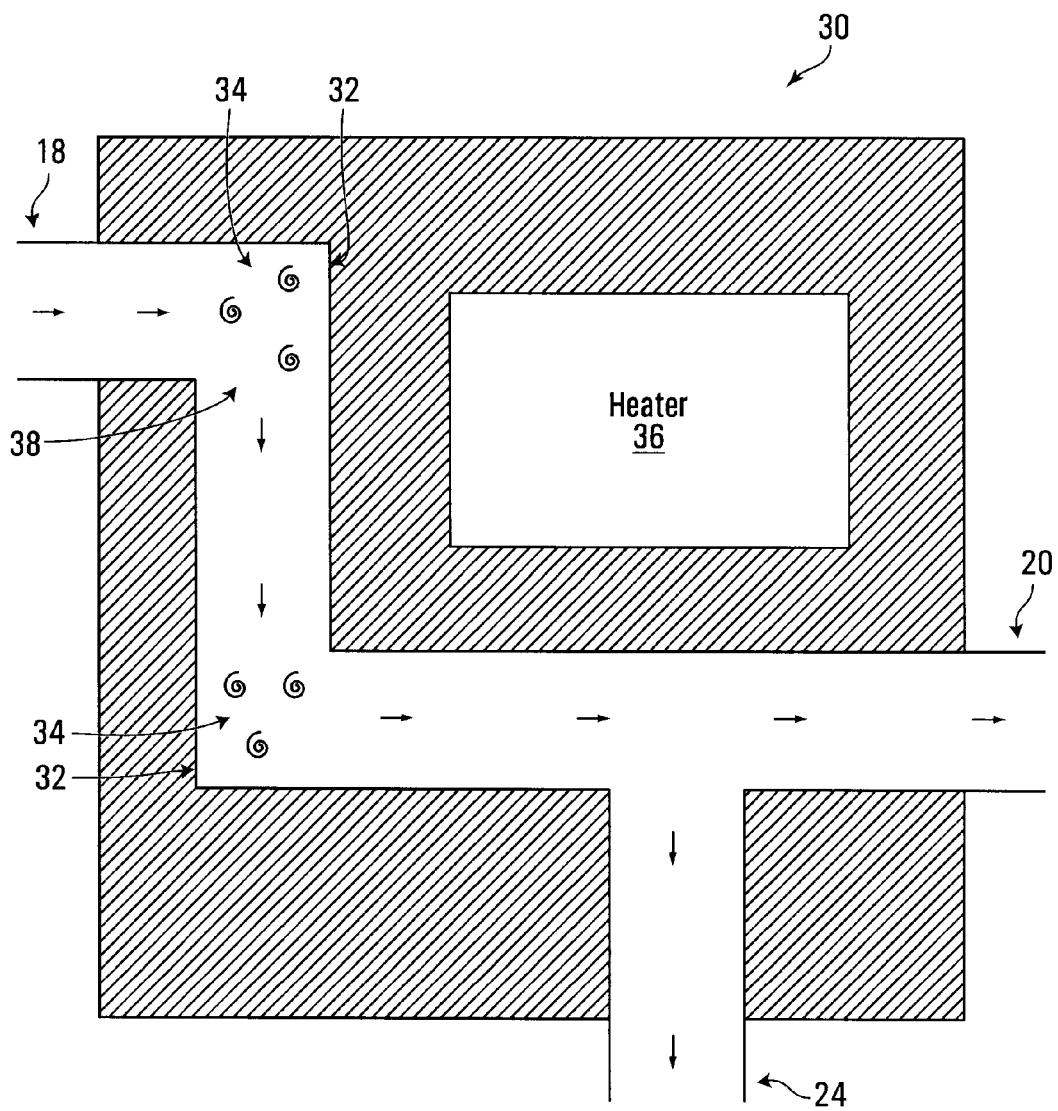
FIG. 2 is a schematic diagram of a desorber of the non-contact trace chemical screening device of FIG. 1.

As illustrated in FIG. 2, desorber 30 includes a desorber inlet 18 for receiving airflow entraining analyte from the detection area, a desorption channel 38 through which airflow passes, a desorber waste outlet 20 for exhausting waste airflow out of desorber 30, and a heater 36 for heating airflow traveling through desorption channel 38 to effect thermal desorption of molecules from analyte entrained in the airflow.

Desorption channel 38 is enclosed by sidewalls, creating a substantially or completely sealed path through which airflow travels. The path created by desorption channel 38 has a cross-sectional area of approximately 0.8 mm$^2$ to 135 mm$^2$, and preferably between 1.5 mm$^2$ to 10 mm$^2$. In some embodiments, the cross-sectional area of desorption channel 38 may vary along its length. The path created by desorption channel 38 path has a length of approximately 50 mm to 200 mm, and preferably between 80 mm to 120 mm.

Desorption channel 38 may include one or more bends 32 to induce desorption through collision of analyte entrained the airflow. Bends 32 typically have an angle of 90 degrees, but other sharp angles suitable for inducing desorption through collisions may also be used.

Desorber 30 is designed to cause a sufficient quantity of molecules to desorb from the analyte to enable mass spectrometer 50 to detect the target substance. Desorption in desorber 30 increases the concentration of vapour molecules of the target substance a level above the sensitivity threshold of mass spectrometer 50. Consequently, desorber 30 does not include a preconcentrator to accumulate analyte molecules for detection over time. This allows airflow to travel from package 14 through desorber 30 to mass spectrometer 50 without interruption.

Heater 36 is selected to heat desorption channel 38 to effect thermal desorption. A suitable range for the temperature of the airflow in the desorption channel 28 to effect thermal desorption is 80° C. to 300° C., and preferably between 150° C. to 250° C. Heater 36 may of a conventional variety, such as the Watlow® FireRod® heater, which operates at approximately 100 watts to 1000 watts, and preferably between 200 watts to 300 watts.

In some embodiments, desorber 30 may include additional spaced-apart heaters (not shown) along the length of desorption channel 38. Multiple heaters may be used to improve the temperature profile along the length of desorption channel 38.

Figure 3:
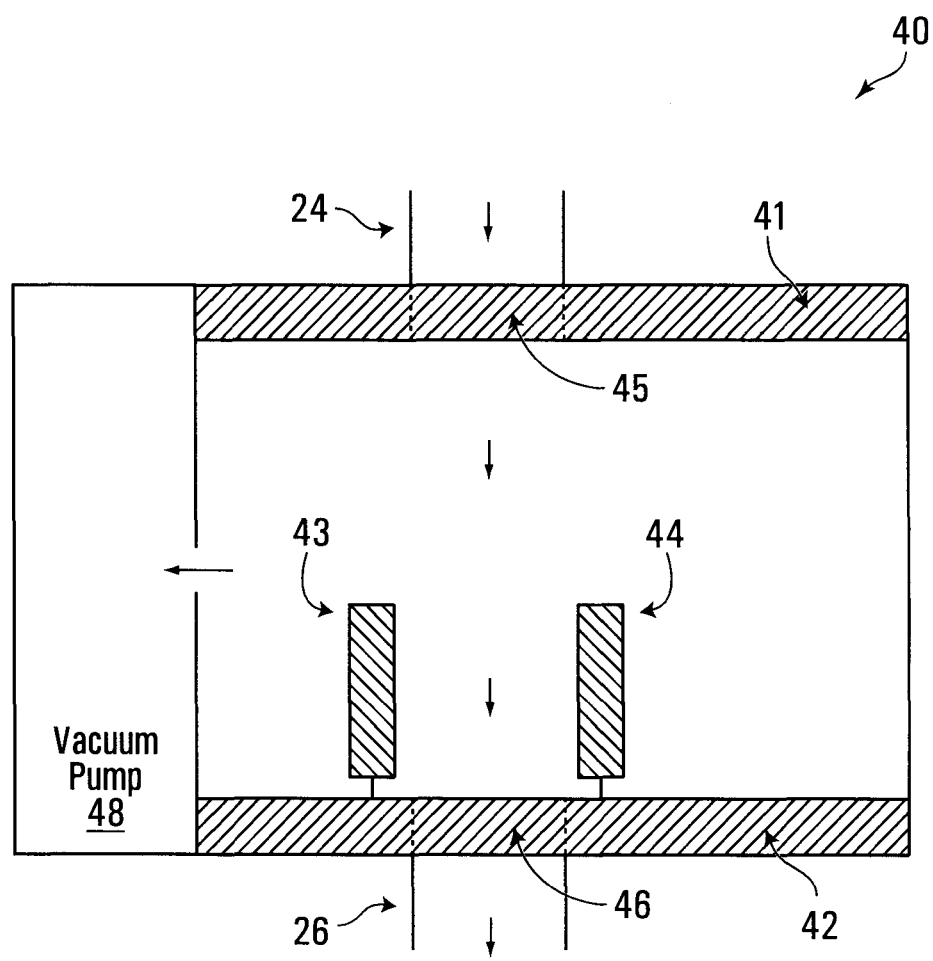
FIG. 3 is a schematic diagram of a glow discharge ionizer of the non-contact trace chemical screening device of FIG. 1.

As illustrated in FIG. 3, ionizer 40 includes primary plates 41 and 42 for forming an ionizing glow discharge, secondary plates 43 and 44, also for forming an ionizing glow discharge, and a vacuum pump 48 for reducing air pressure within ionizer 40. Primary plate 41 has an aperture 45 for receiving airflow from desorber 30 via ionier inlet 24. Similarly, primary plate 44 has an aperture 46 for sending ions to mass spectrometer 50 via mass spectrometer inlet 26. Aperture 45 has a diameter of approximately 100 μm to 500 μm, while aperture 46 has a diameter of approximately 600 µm to 1000 µm. In some embodiments, the diameters of apertures 45 and 46 may be adjustable.

Ionizer inlet 24 may include a pump (not shown) for drawing air through ionizer inlet 24. Ionizer inlet 24 may further include a filter (not shown) to prevent solid particles, water vapour molecules, or other unwanted substances from entering ionizer 40.

Ionizer 40 ionizes vapour molecules entrained in the portion of the airflow entering via ionizer inlet 24 using an ionization method commonly known as glow discharge ionization, as described, for example, in Scott A. McLuckey et al., "Atmospheric Sampling Glow Discharge Ionization Source for the Determination of Trace Organic Compounds in Ambient Air", Analytical Chemistry, Vol. 60, No. 20, Oct. 14, 1988, pp. 2220-2227, and U.S. Pat. No. 4,849,628 to McLuckey et al. The contents of both documents are hereby incorporated by reference.

In an alternate embodiment, ionizer 40 may be replaced with an ionizer performing ionization according to other ionization methods. In an alternate embodiment, ionizer 40 may be replaced with an ionizer producing ions according to a chemical ionization method, as described in U.S. Pat. No. 6,037,587 to Dowell et al., the contents of which are hereby incorporated by reference. According to this chemical ionization method, ions are produced by colliding vapour molecules with ions of a reagent gas.

In a another alternate embodiment, ionizer 40 may be replaced with an ionizer producing ions according to electron ionization (also known as electron impact ionization), as described, for example, in Jürgen Gross, *Mass Spectrometry: A Textbook,* 2nd ed., Springer, 2011, the contents of which are hereby incorporated by reference. According to this electron ionization method, ions are formed by impacting vapour molecules with energized electrons within an electron beam.

In another alternate embodiment, ionizer 40 may be replaced with an ionizer producing ions according to corona discharge ionization, as described in U.S. Pat. No. 7,326,926 to Wang, the contents of which are hereby incorporated by reference. According to this corona discharge ionization method, ions are produced by creating a potential difference of a few thousand volts between two electrodes. This potential difference ionizes vapour molecules surrounding the electrodes, resulting in a corona discharge.

A person skilled in the art will understand that ionizer 40 may be replaced with other known ionizers capable of ionizing vapour molecules carried in the airflow.

Figure 4:
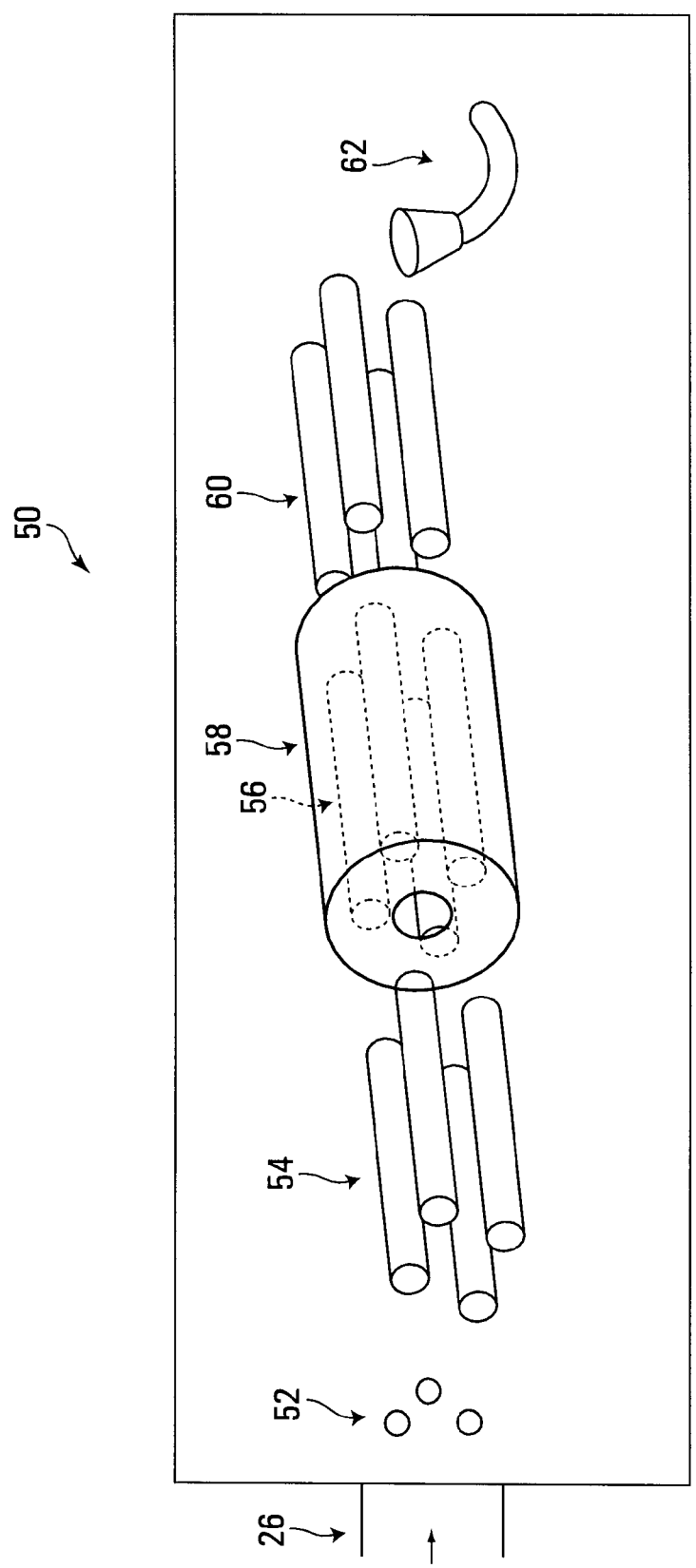
FIG. 4 is a schematic diagram of a mass spectrometer of the non-contact trace chemical screening device of FIG. 1

As illustrated in FIG. 4, mass spectrometer 50 includes a mass spectrometer inlet 26 for receiving ions from ionizer 40, a first quadrupole 54 for performing mass filtering, a second quadrupole 56 in a collision chamber 58 for fragmenting ions, a third quadrupole 60 for performing further mass filtering, and a detector 62 for analyzing ions and ion fragments to detect the target substance.

Mass spectrometer 50 may also include a communication interface (not shown) to facilitate communication with an interconnected computer. The communication interface may operate according to USB, RS-232, Ethernet, Wi-Fi™ or any similar interface capable of transmitting and receiving data between mass spectrometer 50 and an interconnected computer. The interconnected computer may be remotely-located and communicate with mass spectrometer 50 over a communication network. The communication network may be wired and/or wireless.

Mass spectrometer 50 analyzes ions entrained in the airflow entering via mass spectrometer inlet 26. Mass spectrometer 50 may be a tandem mass spectrometer, as described, for example, in Edmond de Hoffmann, "Tandem Mass Spectrometry: a Primer", J. Mass. Spectrometry, Vol. 31, 129-137 (1996), the contents of which are hereby incorporated by reference. More particularly, mass spectrometer 50 may be a triple quadrupole tandem mass spectrometer, as depicted in FIG. 4. A conventional triple quadrupole tandem mass spectrometer, such as the Ionics 3Q Molecular Analyzer™ mass spectrometer from Ionics Mass Spectrometry Group™ may be used.

In an alternate embodiment, mass spectrometer 50 may be replaced with a different type of spectrometer, such as an ion trap mass spectrometer, a time-of-flight mass spectrometer, or an ion mobility spectrometer. Ion trap mass spectrometers and time-of-flight mass spectrometers are described, for example, in Jürgen Gross, *Mass Spectrometry: A Textbook,* 2nd ed., Springer, 2011. Ion mobility spectrometers are described, for example, in Gary Alan Eiceman and Zeev Karpas, *Ion mobility spectrometry,* 2nd ed., CRC Press, 2005, the contents of which are hereby incorporated by reference.

Multiple spectrometers may be further combined to increase sensitivity or selectivity. For example, in an alternate embodiment, mass spectrometer 50 may be replaced with a time-of-flight mass spectrometer combined with an ion trap mass spectrometer.

Any spectrometer or combination of spectrometers may be used so long it provides sufficient sensitivity and selectivity to detect the target substance from the quantity of analyte carried by the airflow without interruption from package 14 through desorber 30 and ionizer 40 to mass spectrometer 50.

Non-contact trace chemical screening device 10, as depicted in FIGS. 1-4, may be operated as follows.

As depicted in FIG. 1, conveyer belt 28 carries package 14 into a detection area within device 10 within range of air jets 12. Conveyer belt 28 may carry package 14 at a speed of approximately 50 cm/s to 200 cm/s. Conveyer belt 28 may carry package 14 through the detection area without stopping, or alternatively, may pause temporarily to keep package 14 within the detection area for a sufficient duration to allow device 10 to detect the target substance.

While luggage 14 is in the detection area, air blown from one or more of air jets 12 strikes the surface of package 14 to create air disturbances 16. Air disturbances 16 lift analyte from the surface of package 14 into an airflow, which immediately entrains the lifted analyte. Analyte may contain residues of the target substance in particle or vapour form.

Air jets 12 may be operated to blow air in a continuous or pulsed fashion. In embodiments including more than one air jet 12, air jets 12 may be operated concurrently or in a predetermined sequence. Operation of air jets 12 is configured to maximize the quantity of analyte lifted from the surface of package 14 and then entrained in the airflow.

Airflow carrying analyte is received by desorber 30 from the detection area via desorber inlet 18. To cause a sufficient quantity of molecules of the target substance to desorb from the analyte for detection, fan 22 draws airflow through desorber 30 at a rate of approximately 10 L/min to 100 L/min, and preferably between 10 L/min to 20 L/min. For detection of the target substance on each package such as package 14, approximately 0.1 L to 2 L, preferably 0.1 L to 0.3 L, of air is drawn through desorber 30.

As depicted in FIG. 2, the airflow travels along desorption channel 38 towards ionizer inlet 24 and desorber waste outlet 20. While the airflow travels along desorption channel 38, it is heated by heater 36. Heating increases the volatility of analyte entrained in the airflow and thereby causes molecules to desorb from the analyte.

As the airflow travels along desorption channel 38, it strikes the wall of desorption channel 38 at sharp bends 32 to create collisions 34 resulting in heated airflow molecules. Collisions 34 between analyte and molecules in the airflow, and between analyte and the wall of desorption channel 38 causes further molecules to desorb from the analyte entrained in the airflow.

While airflow travels along desorption channel 38, desorption channel 38 causes a sufficient quantity of molecules to desorb from the analyte in the airflow to enable mass spectrometer 50 to detect the target substance.

As molecules desorb from analyte entrained in the airflow traveling through desorption channel 38, the molecules also become entrained in the airflow. A portion of this airflow, entraining vapour molecules, enters ionizer 40 through ionizer inlet 24 at a rate of approximately 0.3 L/min to 1.5 L/min, and preferably between 0.8 L/min to 1.2 L/min. The remainder of the airflow is drawn out of desorber 30 through desorber waste outlet 20 as exhaust airflow by fan 22, as shown in FIG. 1.

As depicted in FIG. 3, the portion of the airflow carrying vapour molecules enters ionizer inlet 24 and travels through ionizer 40 towards mass spectrometer inlet 26.

Vacuum pump 48 draws air out of ionizer 40 to reduce air pressure within ionizer 40 to between approximately 10 Pa and 300 Pa. A glow discharge is formed by operating ionizer 40 in one of two modes. In the first mode, a voltage difference of approximately 300 V to 500 V is created between primary plates 41 and 42. This voltage difference may be achieved, for example, by applying approximately −400 V to primary plate 41 and either approximately −10 V to primary plate 42 when negative ions are desired, or approximately 10 V to primary plate 42 when positive ions are desired. This voltage difference produces a glow discharge which ionizes vapour molecules between primary plates 41 and 42. In the second mode, a voltage difference of approximately 300 V to 500 V is created between secondary plates 43 and 44, for example by applying approximately 200 V to secondary plate 43 and approximately −200 V to secondary plate 44. This voltage difference produces a glow discharge which ionizes vapour molecules between secondary plates 43 and 44. Ions formed by the glow discharge are then carried in airflow out of ionizer 40 through mass spectrometer inlet 26 into mass spectrometer 50.

Mass spectrometer 50, as depicted in FIG. 4, analyzes positive and negative ions from ionizer 40 detect the target substance.

First quadrupole 54 performs mass filtering of ions 52 to select a subset of ions based on specified m/z values. Second quadrupole 56 then fragments a portion of the selected ions to form fragment ions. Third quadrupole 60 then performs mass filtering of unfragmented ions and fragment ions to select a further subset of unfragmented ions and fragment ions based on specified m/z values. Detector 62 then performs mass analysis on this further subset of unfragmented ions and fragment ions. Based on this mass analysis, detector 62 determines if the target substance is present.

In embodiments of mass spectrometer 50 with a communication interface, mass spectrometer 50 may communicate with an interconnected computer. This communication interface may be used to program mass spectrometer 50 to detect a particular target substance by specifying the m/z values to filter for the target substance, and by specifying the mass spectrum for the target substance. Mass spectrometer 50 may also be programmed to sequentially detect multiple target substances in analyte lifted from a single subject such as package 14. This communication interface may also be used to communicate detection results to the interconnected computer.

In the embodiment of non-contact trace chemical screening device 10 depicted in FIGS. 1-4, airflow carrying analyte travels without interruption from package 14 to mass spectrometer 50 in approximately 500 milliseconds to 2000 milliseconds. The total screening time for package 14, including travel time of the airflow from package 14 to mass spectrometer 50, is approximately 600 milliseconds to 2100 milliseconds.

Figure 5B:
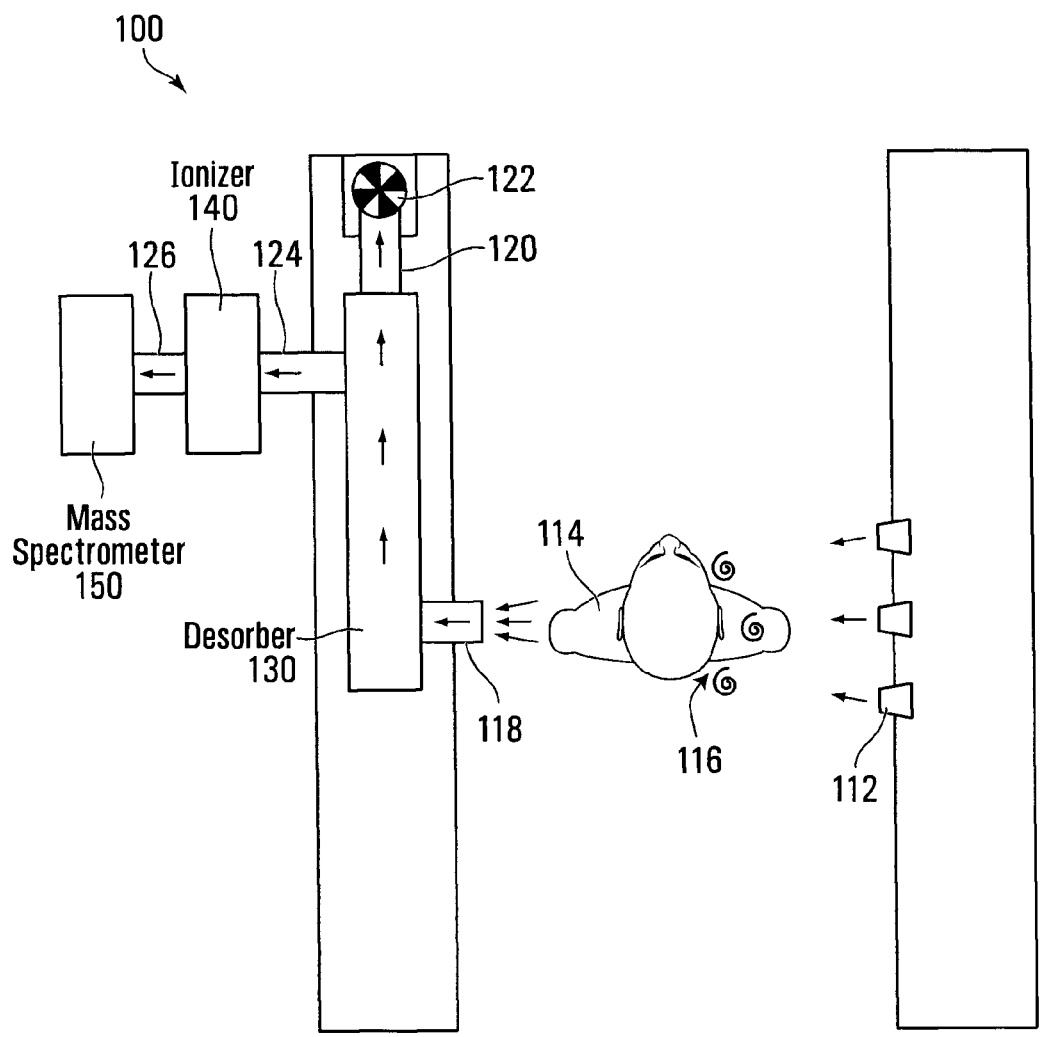
FIG. 5B is a schematic diagram of the non-contact trace chemical screening device of FIG. 5A.

FIGS. 5A and 5B show a non-contact trace chemical screening device 100, exemplary of another embodiment of the present invention. Device 100 may be used to detect a target substance on persons such as person 114.

As illustrated in FIG. 5B, device 100 includes a plurality of air jets 112 for blowing analyte from person 114 that become entrained in an airflow; a desorber 130 for desorbing molecules from analyte carried in the airflow from desorber inlet 118; a fan 122 for drawing the airflow through desorber 130, and for exhausting waste airflow from desorber 130 out of device 100; an ionizer 140 for ionizing vapour molecules in a portion of airflow received from desorber 130; and a mass spectrometer 150 for analyzing ions in the portion of airflow received from ionizer 140 to detect the target substance.

Device 100 may include a turnstile or gate (not shown) to restrict movement of person 114 through device 100.

In operation, person 114 walks through a detection area in device 100. Person 114 may be stopped within the detection area for a sufficient duration to allow device 100 to perform detection of the target substance.

While person 114 is in the detection area, one or more air jets 112 blows air towards person 114 to create air disturbances 116 on the skin and clothing of person 114. Air disturbances 116 lift analyte from the skin and clothing of person 114 into an airflow, which entrains the analyte.

Device 100 detects the target substance in entrained analyte from person 114 using desorber 130, ionizer 140, mass spectrometer 150 and fan 122 in substantially the same way as described above for device 10 using corresponding desorber 30, ionizer 40, mass spectrometer 50 and fan 22.

Figure 6A:
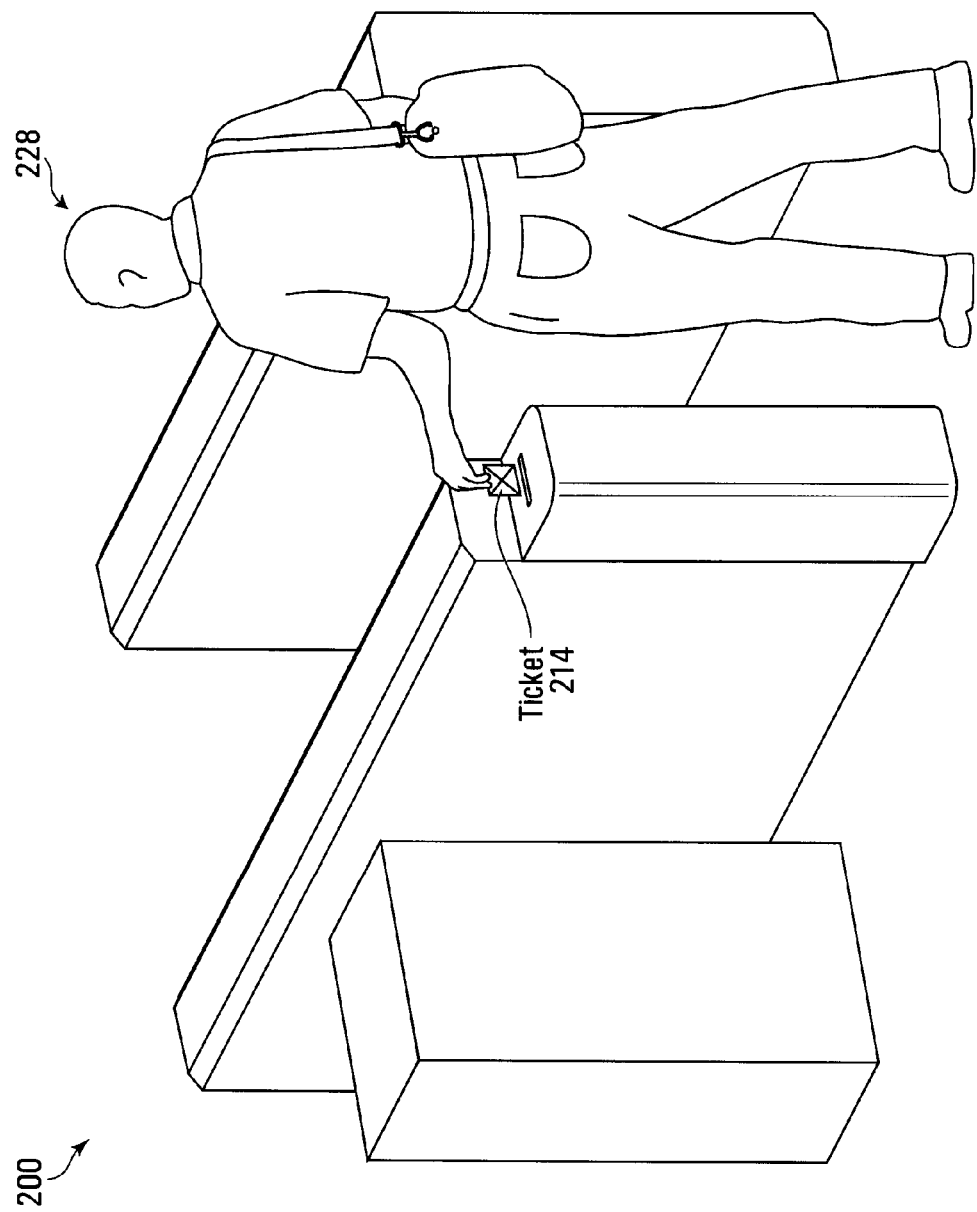
FIG. 6A is a perspective view of a non-contact trace chemical screening device for detecting a target substance on a ticket, exemplary of another embodiment of the present invention.
Figure 6B:
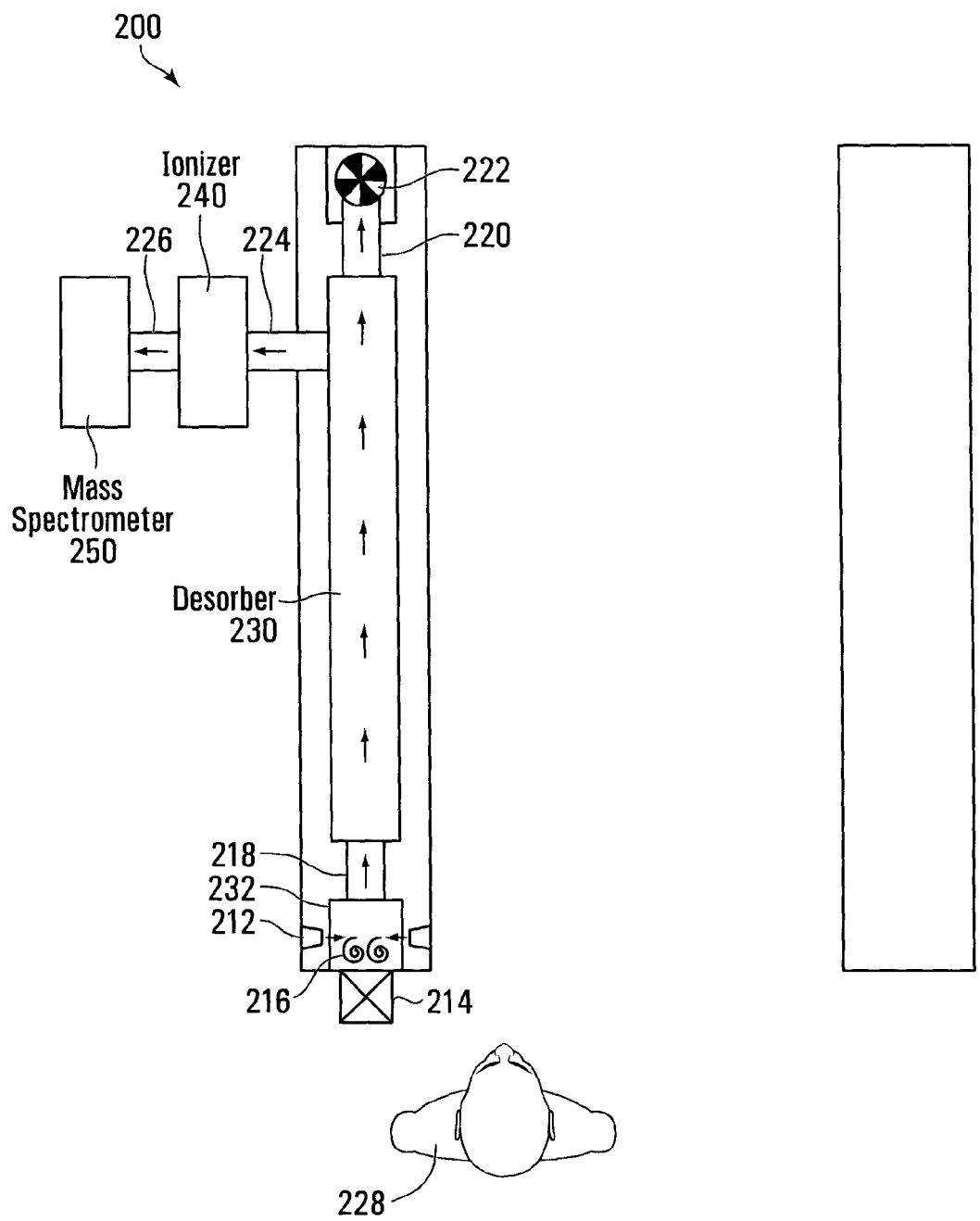
FIG. 6B is a schematic diagram of the non-contact trace chemical screening device of FIG. 6A.

FIGS. 6A and 6B show a non-contact trace chemical screening device 200, exemplary of yet another embodiment of the present invention. Device 200 may be used to detect a target substance on tickets such as ticket 214 carried by person 218.

As illustrated in FIG. 6B, device 200 includes a ticket slot 232 for receiving ticket 214; a plurality of air jets 212 for blowing analyte from ticket 214 into an airflow while it is inserted into ticket slot 232; a desorber 230 for desorbing molecules from analyte carried in the airflow; an ionizer 240 for ionizing vapour molecules in a portion of airflow received from desorber 230; a fan 222 for drawing the airflow through desorber 230, and for exhausting waste airflow from desorber 230 out of device 200; and a mass spectrometer 250 for analyzing ions in the portion of airflow received from ionizer 240 to detect the target substance.

Ticket slot 232 may include a ticket reader (not shown) such as a bar code reader, a magnetic stripe reader, or an integrated chip reader to read information from ticket 214. Ticket slot 232 may also include a ticket validator to validate ticket 214 based on the information read. Ticket 214 may be an airplane boarding pass, such as would be used by person 228 during check-in at an airport. Ticket 214 may also be a subway ticket, an entry ticket for an entertainment facility, or the like.

In operation, person 228 inserts ticket 214 into ticket slot 232. While ticket 214 is inserted into ticket slot 232, one or more air jets 212 blows air towards ticket 214 to create air disturbances 216 on the surface of the ticket 214. Air disturbances 216 lift analyte from the surface of the ticket 214 into an airflow, which entrains the analyte.

Device 200 detects the target substance in entrained analyte from ticket 214 using desorber 230, ionizer 240, mass spectrometer 250 and fan 222 in substantially the same way as described above for device 10 using corresponding desorber 30, ionizer 40, mass spectrometer 50 and fan 22.

In embodiments of ticket slot 232 including a ticket reader, the ticket reader may read information from ticket 214 while device 200 performs detection of the target substance. Additionally, information read from ticket 214 may allow ticket 214 to be validated and/or person 228 to be identified while target substance is detected by device 200.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

Other features, benefits and advantages of the embodiments described herein not expressly mentioned above can be understood from this description and the drawings by those skilled in the art.

What is claimed is:

1. A device for detecting a target substance on a subject without contacting said subject, said device comprising:
    at least one air jet for blowing analyte from a surface of said subject into an airflow, said airflow entraining said analyte;
    a desorber comprising:
        an inlet for receiving at least a portion of said airflow including entrained analyte;
        a desorption channel in fluid communication with said inlet for desorbing molecules from analyte entrained in said portion of said airflow received by way of said inlet, and travelling through said desorption channel;
    an ionizer, in fluid communication with said desorption channel, for forming ions from vapour molecules in said portion of said airflow;
    at least one mass spectrometer in fluid communication with said ionizer, for analyzing said ions to detect said target substance;
    wherein said airflow travels without interruption from said subject to said at least one mass spectrometer; and
    wherein said desorption channel causes a sufficient quantity of molecules to desorb from said analyte to enable said at least one mass spectrometer to detect said target substance.

2. The device of claim 1, wherein said airflow travels from said subject to said mass spectrometer in less than 2000 milliseconds.

3. The device of claim 2, wherein said detecting is performed in less than 2100 milliseconds.

4. The device of claim 1, wherein less than 2 liters of said airflow travels through said desorption channel during said detecting.

5. The device of claim 1, wherein said at least one air jet is pulsed.

6. The device of claim 1, wherein said desorption channel comprises a heater for effecting thermal desorption.

7. The device of claim 6, wherein said desorption channel comprises at least one bend for effecting desorption by collision of analyte.

8. The device of claim 1, wherein said ionizer forms both positive and negative ions.

9. The device of claim 1, wherein said ionizer forms ions by creating a potential difference between at least two electrodes.

10. The device of claim 9, wherein said ionizer forms ions at or below atmospheric pressure.

11. The device of claim 10, wherein said ionizer is at least one of a corona discharge ionizer; an electron impact ionizer; or a glow discharge ionizer.

12. The device of claim 1, wherein said at least one mass spectrometer analyzes both positive and negative ions in said analyte from said subject.

13. The device of claim 12, wherein said at least one mass spectrometer comprises a tandem quadrupole mass spectrometer.

14. The device of claim 13, wherein said tandem quadrupole mass spectrometer is a triple tandem quadrupole mass spectrometer.

15. The device of claim 13, wherein said tandem quadrupole mass spectrometer comprises at least one quadrupole for fragmenting ions.

16. The device of claim 15, wherein said tandem quadrupole mass spectrometer analyzes fragmented ions.

17. The device of claim 1, wherein results of said detecting may be monitored remotely over a network.

18. The device of claim 1, wherein said subject is at least one of a human being; a parcel; a piece of luggage; a ticket; or a boarding pass.

19. The device of claim 1, wherein said device comprises a conveyer belt for moving said subject into the range of said at least one air jet.

20. A method of detecting a target substance on a subject without contacting said subject, said method comprising:
    blowing analyte from a surface of said subject into an airflow, said airflow entraining said analyte;
    desorbing molecules from said analyte in said airflow, while said airflow travels without interruption from said subject to a tandem quadrupole mass spectrometer;
    ionizing vapour molecules in said airflow to form ions; and
    analyzing said ions using at least one mass spectrometer to detect said target substance.

21. The method of claim 20, wherein said airflow travels from said subject to said at least one mass spectrometer in less than 2000 milliseconds.

22. The method of claim 21, wherein said detecting is performed in less than 2100 milliseconds.

23. The method of claim 20, wherein less than 2 liters of said airflow travels through a desorption channel during said detecting.

24. The method of claim 20, wherein said method further comprises heating a portion of said airflow travelling through a desorption channel to effect thermal desorption.

25. The method claim 20, wherein said method further comprises effecting desorption by collision of analyte.

26. The method of claim 20, wherein said method further comprises fragmenting said ions to form fragment ions.

27. The method of claim 26, wherein said method further comprises analyzing said fragment ions using said at least one mass spectrometer to detect said target substance.

* * * * *